US00PP22126P2

(12) United States Plant Patent
Niederländer

(10) Patent No.: US PP22,126 P2
(45) Date of Patent: Sep. 6, 2011

(54) ***ASTER* PLANT NAMED 'KIASTLAVMI'**

(50) Latin Name: *Aster dumosus*
Varietal Denomination: Kiastlavmi

(75) Inventor: Andreas Niederländer, Gensingen (DE)

(73) Assignee: Kientzler Jungpflazen GmbH & Co. KG, Gensingen (DE)

( * ) Notice: Subject to any disclaimer, the term of this patent is extended or adjusted under 35 U.S.C. 154(b) by 0 days.

(21) Appl. No.: 12/807,629

(22) Filed: Sep. 9, 2010

(51) Int. Cl.
*A01H 5/00* (2006.01)

(52) U.S. Cl. ..... Plt./355

(58) Field of Classification Search ..... Plt./355
See application file for complete search history.

*Primary Examiner* — Kent L Bell
(74) *Attorney, Agent, or Firm* — C. A. Whealy

(57) ABSTRACT

A new and distinct cultivar of *Aster* plant named 'Kiastlavmi', characterized by its compact, upright, uniform and mounded plant habit; freely branching growth habit; semi-double type inflorescences with violet-colored ray florets; and tolerance to mildew.

1 Drawing Sheet

Botanical designation: *Aster dumosus*.

Cultivar denomination: 'KIASTLAVMI'.

BACKGROUND OF THE INVENTION

The present invention relates to a new and distinct cultivar of *Aster* plant, botanically known as *Aster dumosus* and hereinafter referred to by the name 'Kiastlavmi'.

The objective of the breeding program is to create new compact *Aster* plants with uniform growth habit, freely branching habit, attractive and numerous ray florets and tolerance to mildew.

The new *Aster* plant originated from a cross-pollination in 2005, in Gensingen, Germany of *Aster dumosus* 'Kristina', not patented, as the female, or seed, parent with a proprietary selection of *Aster dumosus* identified as code number 08-15-4711, not patented, as the male, or pollen, parent. The new *Aster* plant was discovered and selected by the Inventor as a single flowering plant within the progeny of the stated cross-pollination in a controlled greenhouse environment in Gensingen, Germany in September, 2006.

Asexual reproduction of the new *Aster* plant by vegetative tip cuttings was first conducted in a controlled greenhouse environment in Gensingen, Germany in 2007. Asexual reproduction by vegetative tip cuttings has shown that the unique features of this new *Aster* plant are stable and reproduced true to type in successive generations.

SUMMARY OF THE INVENTION

Plants of the new *Aster* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Kiastlavmi'. These characteristics in combination distinguish 'Kiastlavmi' as a new and distinct *Aster* plant:

1. Compact, upright, uniform and mounded plant habit.
2. Freely branching growth habit.

3. Semi-double type inflorescences with violet-colored ray florets.
4. Tolerance to mildew.

Plants of the new *Aster* differ from plants of the female parent, 'Kristina', in the following characteristics:

1. Plants of the new *Aster* are more compact than plants of 'Kristina'.
2. Plants of the new *Aster* are more rounded than plants of 'Kristina'.
3. Plants of the new *Aster* and 'Kristina' differ in ray floret color as plants of 'Kristina' have white-colored ray florets.

Plants of the new *Aster* differ from plants of the male parent selection in the following characteristics:

1. Plants of the new *Aster* are smaller than plants of the male parent selection.
2. Plants of the new *Aster* flower earlier than plants of the male parent selection.
3. Plants of the new *Aster* and male parent selection differ in ray floret color as plants of male parent selection have lighter colored ray florets.

Plants of the new *Aster* can be compared to plants of 'Sapphire', not patented. In side-by-side comparisons conducted in Gensingen, Germany, plants of the new *Aster* differed from plants of 'Sapphire' in the following characteristics:

1. Plants of the new *Aster* were more compact than plants of 'Sapphire'.
2. Plants of the new *Aster* and 'Sapphire' differed in ray floret color as plants of 'Sapphire' had lighter colored ray florets.

Plants of the new *Aster* can be compared to plants of 'Professor Anton Kippenberg', not patented. In side-by-side comparisons conducted in Gensingen, Germany, plants of the new *Aster* differed from plants of 'Professor Anton Kippenberg' in the following characteristics:

1. Plants of the new *Aster* were more compact than plants of 'Professor Anton Kippenberg'.
2. Inflorescences of plants of the new *Aster* had more ray florets than inflorescences of plants of 'Professor Anton Kippenberg'.

3. Plants of the new *Aster* and 'Professor Anton Kippenberg' differed in ray floret color as plants of 'Professor Anton Kippenberg' had lighter colored ray florets.

BRIEF DESCRIPTION OF THE PHOTOGRAPHS

The accompanying photographs illustrate the overall appearance of the new *Aster* plant. These photographs show the colors as true as it is reasonably possible to obtain in colored reproductions of this type. Colors in the photographs may differ slightly from the color values cited in the detailed botanical description which accurately describe the colors of the new *Aster* plant.

The photograph at the bottom of the sheet comprises a side perspective view of a typical flowering plant of 'Kiastlavmi' grown in a container.

The photograph at the top of the sheet is a close-up view of a typical flowering plant of 'Kiastlavmi'.

DETAILED BOTANICAL DESCRIPTION

The aforementioned photographs and following observations and measurements describe plants grown in 10-cm containers during the summer in an outdoor nursery in Loudon, N.H. and under conditions and practices which approximate those generally used in commercial potted *Aster* production. During the production of the plants, day temperatures ranged from 21° C. to 32° C. and night temperatures ranged from 7° C. to 18° C. Plants were pinched one time and were ten weeks old when the photographs and description were taken. In the following description, color references are made to The Royal Horticultural Society Colour Chart, Fifth Edition, 2007, except where general terms of ordinary dictionary significance are used.

Botanical classification: *Aster dumosus* 'Kiastlavmi'.

Parentage:

*Female, or seed, parent.*—*Aster dumosus* 'Kristina', not patented.

*Male, or pollen, parent.*—Proprietary selection of *Aster dumosus* identified as code number 08-15-4711, not patented.

Propagation:

*Type.*—Terminal vegetative cuttings.

*Time to initiate roots, summer.*—About six to eight days at temperatures of 18° C. to 20° C.

*Time to initiate roots, winter.*—About eight to twelve days at temperatures of 18° C. to 20° C.

*Time to produce a rooted young plant, summer.*—About 18 days at average temperatures of 18° C. to 20° C.

*Time to produce a rooted young plant, winter.*—About 22 days at average temperatures of 18° C. to 20° C.

*Root description.*—Fine, fibrous; white in color.

*Rooting habit.*—Moderately freely branching; moderately dense.

Plant description:

*Appearance.*—Semi-double type Aster; compact and upright growth habit; inverted triangle with uniformly mounded crown; freely branching growth habit with about three primary lateral branches each with about six to eight secondary lateral branches; dense and full plants; vigorous growth habit.

*Plant height.*—About 25 cm.

*Plant width.*—About 31 cm.

*Lateral branches.*—Length, primary lateral branches: About 25 cm. Length, secondary lateral branches: About 16 cm. Diameter: About 4 mm. Internode length: About 1.5 cm. Strength: Strong. Texture, developing stems: Scattered pubescence. Texture, developed stems: Smooth, glabrous. Color: Close to N137A.

Foliage description:

*Arrangement.*—Alternate, simple; sessile.

*Length, lower leaves.*—About 6.7 cm.

*Width, lower leaves.*—About 1.2 cm.

*Shape.*—Oblanceolate.

*Apex.*—Acute.

*Base.*—Attenuate; clasping.

*Margin.*—Entire.

*Texture, upper and lower surfaces.*—Smooth, glabrous.

*Venation pattern.*—Pinnate, reticulate.

*Color.*—Developing leaves, upper surface: Close to 137B. Developing leaves, lower surface: Close to 146B. Fully expanded leaves, upper surface: Close to 137A; venation, close to 146C. Fully expanded leaves, lower surface: Close to 146A; venation, close to 146C.

Inflorescence description:

*Appearance.*—Semi-double type inflorescence form with lanceolate-shaped ray florets; inflorescences terminal and axillary and held above and beyond the foliar plane on strong peduncles; ray and disc florets arranged acropetally on a capitulum.

*Fragrance.*—None detected.

*Flowering response.*—Under natural conditions, plants flower in the late summer through the autumn in the Northern Hemisphere.

*Inflorescence longevity.*—Inflorescences last about five to seven days on the plant; inflorescences persistent.

*Inflorescence bud.*—Height: About 1.5 cm. Diameter: About 8 mm. Shape: Ovoid. Color: Towards the apex, close to 90B; towards the base, close to 155A.

*Inflorescence size.*—Diameter: About 3.8 cm. Depth (height): About 1.4 cm. Diameter of disc: About 1 cm. Receptacle height: About 8 mm. Receptacle diameter: About 5 mm. Receptacle color: Close to 137B.

*Ray florets.*—Length: About 2.2 cm. Width: About 2 mm. Shape: Lanceolate. Apex: Acute. Base: Attenuate. Margin: Entire. Texture, upper and lower surfaces: Smooth, glabrous. Orientation: Initially upright, then close to perpendicular to peduncle; apices recurve with development. Number of ray florets per inflorescence: About 68 arranged in about three to four whorls. Color: When opening, upper surface: Close to 85A. When opening, lower surface: Close to 85B. Fully opened, upper surface: Close to N87C; color resists fading. Fully opened, lower surface: Close to 85C; color resists fading.

*Disc florets.*—Arrangement: Massed at center of receptacle. Shape: Tubular, elongated. Apex: Five-pointed. Length: About 1.1 cm. Width: About 1.5 mm. Number of disc florets per inflorescence: About 50. Texture: Smooth, glabrous. Color, immature: Apex: Close to 14C. Mid-section: Close to 2C. Base: Close to 2D. Color, mature: Apex: Close to 2D. Mid-section: Close to 11D. Base: Close to 11D.

*Phyllaries.*—Number of phyllaries per inflorescence: About 70 arranged in about four to six whorls. Length: About 5 mm. Width: About 1 mm. Shape: Narrowly lanceolate. Apex: Acute. Base: Truncate.

Margin: Entire. Texture, upper and lower surfaces: Smooth, glabrous. Color, upper and lower surfaces: Close to 137B.

*Peduncles.*—Length, terminal peduncle: About 3.4 cm. Length, fourth peduncle: About 2.8 cm. Length, seventh peduncle: About 5.1 cm. Diameter: About 1 mm. Angle: Upright to 45° from vertical. Strength: Strong, flexible. Texture: Smooth, glabrous. Color: Close to 137B.

*Reproductive organs.*—Androecium: Present on disc florets only. Filament length: About 4 mm. Filament color: Close to 157C. Anther shape: Narrowly elongated. Anther length: About 2 mm. Anther color: Close to 2B. Pollen amount: None observed. Gynoecium: Present on both ray and disc florets. Pistil length: About 7 mm. Stigma shape: Bi-parted. Stigma color: Close to 157B. Style length: About 4 mm. Style color: Close to 157D. Ovary color: Close to NN155B.

*Seed/fruit.*—Seed and fruit production have not been observed.

Disease/pest resistance: Tolerance to mildew has been observed on plants of the new *Aster.* Resistance to pests and other pathogens common to *Asters* has not been observed on plants grown under commercial conditions.

Garden performance: Plants of the new *Aster* have been observed to be rain and wind tolerant and to tolerate temperatures from about 0° C. to about 35° C.

It is claimed:

1. A new and distinct *Aster* plant named 'Kiastlavmi' as illustrated and described.

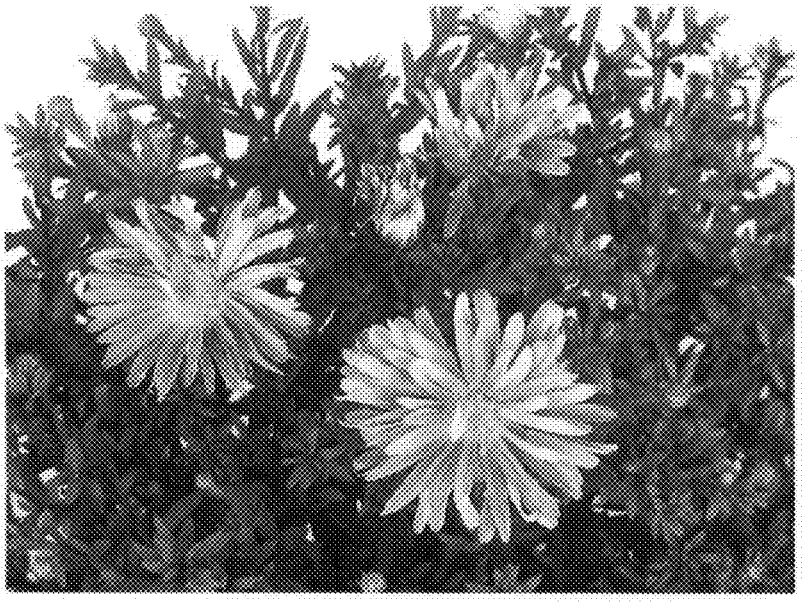
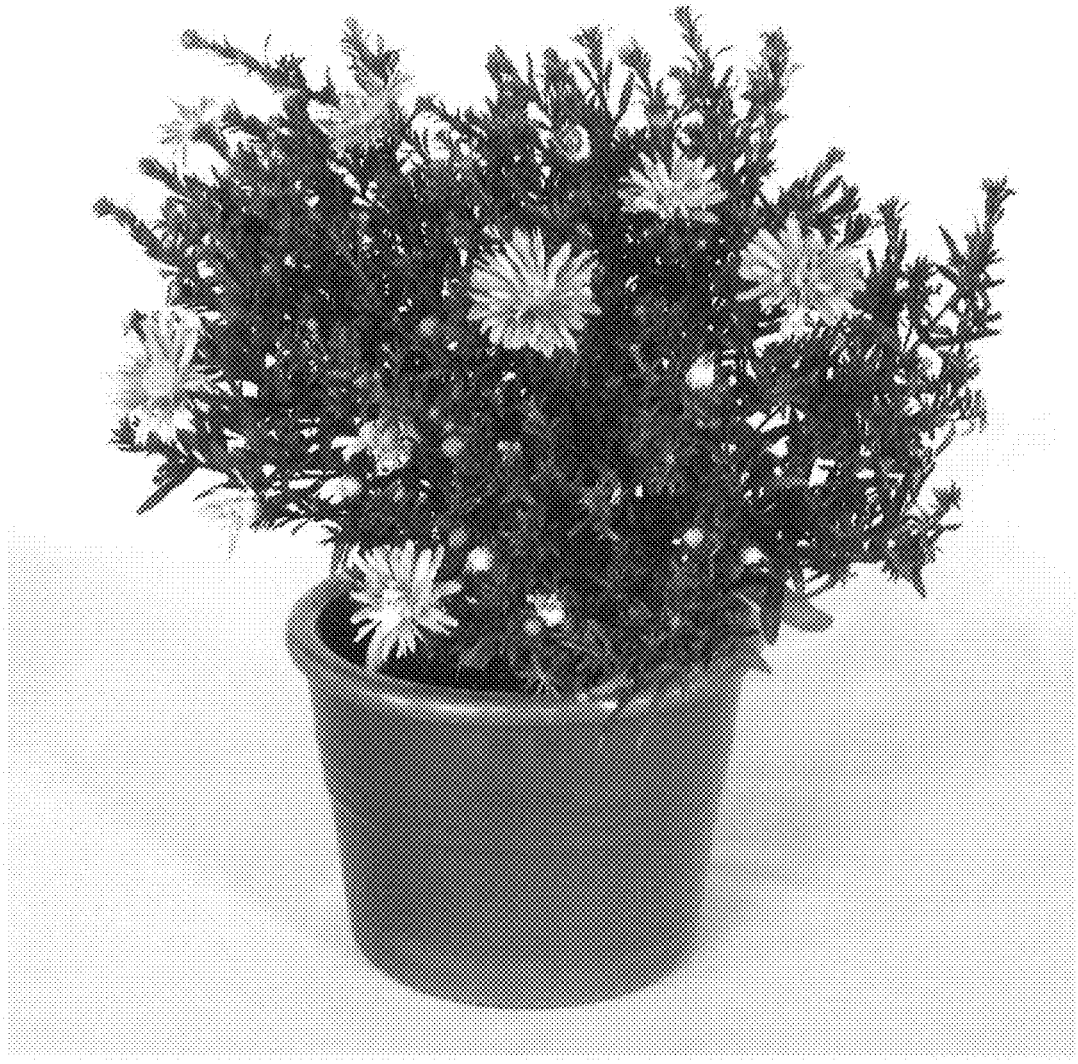

* * * * *